United States Patent [19]

Weiss et al.

[11] Patent Number: 5,474,897
[45] Date of Patent: Dec. 12, 1995

[54] SCREENING ASSAY FOR THE IDENTIFICATION OV NOVEL IMMUNOSUPPRESSIVES USING CULTURED T CELLS

[75] Inventors: Arthur Weiss, Mill Valley; James Fraser, San Francisco, both of Calif.

[73] Assignee: The Regents of the University of California, Oakland, Calif.

[21] Appl. No.: 152,955

[22] Filed: Nov. 15, 1993

Related U.S. Application Data

[63] Continuation of Ser. No. 898,639, Jun. 15, 1992, abandoned.

[51] Int. Cl.$^6$ ..................................................... C12Q 1/68
[52] U.S. Cl. ........................... 435/6; 435/69.1; 435/70.4; 435/240.2
[58] Field of Search ........................... 435/6, 290.2, 704, 435/69.1, 172.1, 172.3

[56] References Cited

U.S. PATENT DOCUMENTS

| | | | |
|---|---|---|---|
| 4,868,112 | 9/1989 | Toole, Jr. | 435/68 |
| 5,053,337 | 10/1991 | Weinshank et al. | 435/290.2 |
| 5,082,774 | 1/1992 | Heinrich | 435/69.1 |

OTHER PUBLICATIONS

Ohashi, P. S. et al. "Reconstruction of an active surface Te/T–cell antigen receptor by DNA transfer." *Nature* vol. 316, No. 6029 pp. 606–609, 15 Aug. 1985.
Saito T. et al., "Specific antigen–Ia activation of transfected human T cells expressing murine Ti αβ–human T3 receptor complexes." *Nature* vol. 35, pp. 125–130, 8 Jan. 1987.
Maxwell, I. H. et al. "Electroporation of Mammalian Cells with a Firefly Luciferase Expression Plasmid" *DNA* vol. 7, No. 8, pp. 557–562, 1988.
Sczakiel, G. et al. "Testing for Electrotransfection Parameters by use of the Fluorescent Dye Lucifer yellow CH." *Analytical Biochemistry* No. 181, pp. 309–314, 1989.
Novak, T. J., et al. "Differential Transient and Long–Term Expression of DNA Sequences Introduced into T–Lymphocyte Lines" *DNA* vol. 5 No. 6, pp. 439–451, 1986.
Kay and Benzie, *Immunol. Letters*, 23, 155–160 (1989).
Sambrook et al., *Molecular Cloning*, Cold Spring Harbor Lab. Press, pp. 16.39–16.40, 1989.

*Primary Examiner*—W. Gary Jones
*Assistant Examiner*—Kenneth r. Horlick
*Attorney, Agent, or Firm*—Townsend and Townsend and Crew

[57] ABSTRACT

A method for identifying compounds capable of inducing immunosuppression by inhibiting the CD28 signal transduction pathway and T cell comprises exposing cultured T cells to one or more test compounds. The T cells are obtained from a T cell line which stably incorporates DNA sequence comprising in reading frame an enhancer region responsive to a CD28-regulated nuclear binding protein and a marker gene. The cells are cultured under conditions which result in activation of both the T cell receptor and the CD28 receptor, resulting in enhanced expression of the marker gene. Test compounds which inhibit expression of the marker gene are considered as candidates for immunosuppressive drugs.

4 Claims, 2 Drawing Sheets

SEQUENCE LISTING ( 1 ) GENERAL INFORMATION:

( i i i ) NUMBER OF SEQUENCES: 5

(2) INFORMATION FOR SEQ ID NO:1:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

AAGAAATTCC A        11

(2) INFORMATION FOR SEQ ID NO:2:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AGGAGATTCC A        11

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TGGAGGTTCC A        11

(2) INFORMATION FOR SEQ ID NO:4:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CAGAGATTCC A        11

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGGAAACTCT A        11

SCREENING ASSAY FOR THE IDENTIFICATION OV NOVEL IMMUNOSUPPRESSIVES USING CULTURED T CELLS

This is a continuation of application Ser. No. 07/898,639 filed Jun. 15, 1992, now abandoned

BACKGROUND OF THE INVENTION

1. Field of the Invention

The present invention relates generally to methods and compositions for identifying immunosuppressive drugs. More particularly, the present invention relates to the identification of drugs which can inhibit T cell-mediated immune response by blocking stimulation of the CD28 signal transduction pathway.

The cellular immune response involves a very complex set of interactions between antigens, T cells, B cells, macrophages, and numerous factors, such as cytokines, which are released by the cells during the course of the interactions. The present invention is concerned particularly with T cell activation which results from interaction with particular antigen presenting cells, such as B cells and macrophages. While specificity of the T cell response is determined by antigen-specific binding to the T cell antigen receptor (TCR), binding to at least one secondary receptor is also necessary for activation. One such secondary receptor is CD28 which, upon stimulation, induces the activity of nuclear proteins which can increase the production of interleukin-2 and possibly other cytokines by binding to an enhancer region associated with the cytokine gens.

Heretofore, most efforts in identifying immunosuppressive drugs which mediate the cellular immune response at the level of intracellular interaction have focused on inhibiting binding to the TCR. While such efforts have met with some success, it would be desirable to provide compositions and methods useful for identifying immunosuppressive drugs which can interfere with binding to secondary T cell receptors, particularly CD28. Such methods should be convenient, inexpensive, rapid, and should permit screening of a large number of candidate drugs under controlled conditions.

2. Description of the Background Art

Weiss et al. (1986) J. Immunol. 137:819–825, describes the ability to activate purified T cells and Jurkat cells by exposure to anti-CD28 antibodies and certain T cell receptor stimulants. Durand et al. (1988) Mol. Cell. Biol. 8:1715–1724, describes the construction of pIL-2-Luc. Fraser et al. (1991) Science 251:313–316, describes the effects of CD28 stimulation on IL-2 enhancer activity in Jurkat cells transiently transfected with pIL-2-Luc. Exposure of the transfected cells to anti-CD28 and TCR stimuli resulted in enhanced luciferase activity. A ligand for stimulating the CD28 receptor present on activated B cells (B7/BB1) is described in Lindsley et al. (1990) Proc. Natl. Acad. Sci. USA 87:5031–5035. The importance of the CD28 costimulatory pathway is described in Fraser et al. (1992) J. Exp. Med. 175:1131–1134.

The full disclosure of each of these references is incorporated herein by reference.

SUMMARY OF THE INVENTION

A method for identifying immunosuppressive compositions comprises administering test compounds to cultured T cells, where the T cells provide a detectable signal when activated via the CD28 receptor. Those test compounds which result in inhibition of the CD28 signal transduction pathway may be further tested for therapeutic effectiveness as immunosuppressive drugs, for use in transplant therapy, for the treatment of autoimmune disorders, and the like.

The T cells are obtained from a T cell line which stably incorporates a DNA sequence comprising an enhancer region responsive to a CD28-regulated nuclear binding protein, a promoter, and a marker gene. The enhancer region is derived from or normally associated with a cytokine gene, such as the enhancer region and promoter for the interleukin-2 (IL-2) gene. The T cells are activated through the T cell receptor (TCR) and are cultured under conditions selected to induce the CD28 signal transduction pathway. Conveniently, TCR activation is mimicked by exposure to ionomycin and phorbol 12-myistate 13-acetate (PMA), or by stimulating cells with anti-TCR antibody or with mitogenic lectins. Induction of the CD28 pathway may be achieved by exposure to anti-CD28 antibody to B7 expressing antigen presenting cells, or to a soluble form of B7 protein.

A particularly useful cell line having one copy of the CD28-enhancer region (CD28RE) is designated Jurkat-IL2-Luc, A.T.C.C. Accession No. CRL 11059.

The present invention further comprises pharmaceutical compositions incorporating immunosuppressive drugs selected by the method described above.

Immunosuppressive drugs which act by suppression of the CD28 pathway may have a number of advantages over drugs which act through other mechanisms. In particular, it is believed that suppression of the CD28 signal transduction pathway while a patient's T cells are subjected to antigen-specific stimulation of the TCR might result in a prolonged antigen-specific immunosuppression, i.e. a form of induced immunotolerance against those antigens which would otherwise induce a cellular response. Thus, it may be possible to identify drugs which provide for an antigen-specific immunosuppression even after their administration is discontinued. The use of such antigen-specific immunosuppressive drugs would be particularly useful in transplant therapy and treatment of autoimmune disorders.

The present invention provides a unique method for identifying drugs which are capable of interfering with or otherwise suppressing the induction of the CD28 signal transduction pathway. In particular, the present invention is able to identify those test compounds which are able to prevent stimulation of the CD28 receptor, e.g. interfere with components of the CD28-signal transduction pathway or less likely with binding of normal CD28 to immunostimulatory factors on antigen presenting B cells, without themselves stimulating the pathway.

DESCRIPTION OF SPECIFIC EMBODIMENTS

Figure 1:
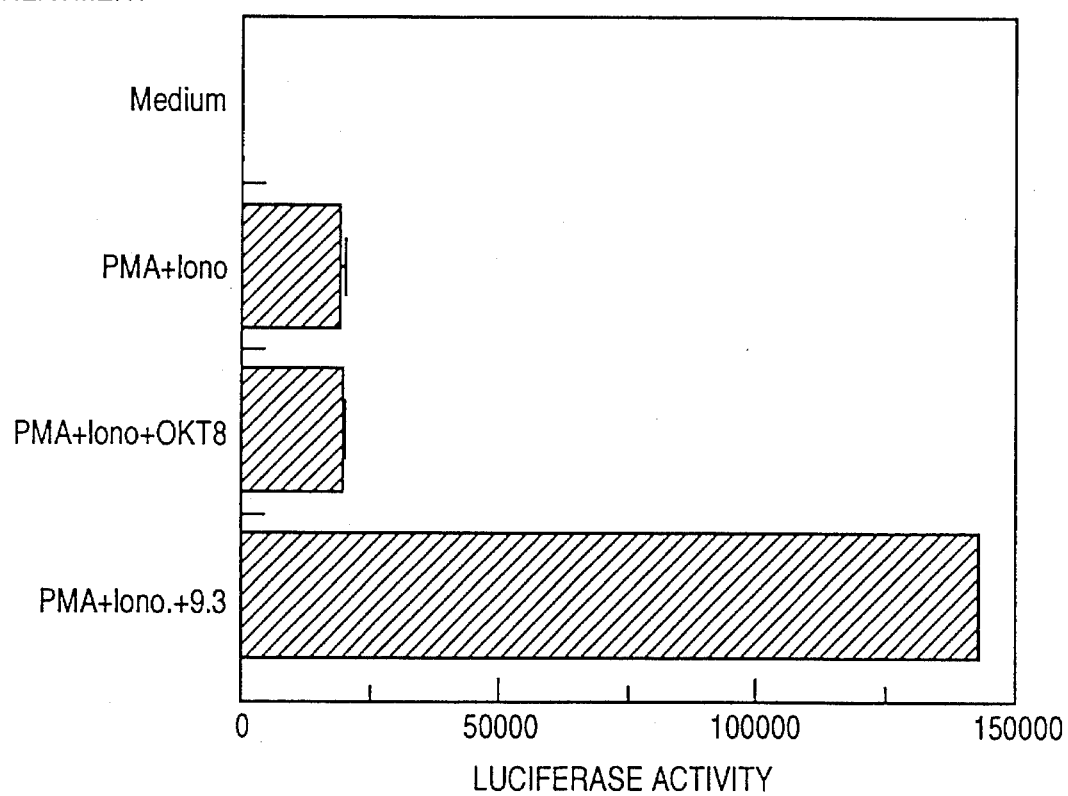
FIG. 1 illustrates the response of the Jurkat-IL2-Luc cell line which stably expresses the plasmid pIL-2-Luc to the indicated stimuli.

According to the present invention, screening assays for immunosuppressive compositions comprise exposing cultured T cells to test compounds, where the T cells produce an observable signal as a result of normal CD28 stimulation. The T cells are cultured under conditions which will, in the absence of effective test compounds, produce the observable signal, generally requiring the presence of substances which result in stimulation of both CD28 and the T cell receptor (TCR). Effective test compounds will be those that at least partially suppress the stimulation of CD28, thus resulting in a decrease in the observable signal.

T cells used in the screening assays of the present invention are obtained from T cell lines which have been modified to stably incorporate a CD28 enhancer region in reading frame with a marker gene so that exposure of the cells to conditions selected to induce the CD28 receptor will result in expression of the marker gene. The T cell lines may be derived by modifying previously established human or mouse T cell lines and hybridomas, where the starting cell lines and hybridomas are capable of expressing certain cytokine gene(s), as discussed below. A variety of cell lines suitable for modification according to the present invention are available from public depositories, such as the American Type Culture Collection (A.T.C.C.), Rockville, Maryland. Exemplary cell lines include Jurkat or HUT-28, human leukemic T cell lines; EL-4, a mouse T cell line; BW5147, a mouse cell line; 2B4, a mouse hybridoma cell line; and human or mouse T cell clones.

The CD28 enhancer region may be derived from the 5'flanking region of a cytokine gene, where the cytokine gene selected should be one which is normally expressed in the cell line being modified. The enhancer region will include at least that portion of the 5'flanking region which is bound by the CD28 nuclear protein which is produced as a result of stimulation of the CD28 receptor, as described below, Suitable enhancer regions may be obtained as set forth in Table 1.

TABLE 1

| Gene | Region | Sequence |
| --- | --- | --- |
| hIL-2 | −162 to −152 | AAGAAATTCCA |
| mIL-2 | −164 to −154 | AAGAAATTCCA |
| hGM-CSF | −96 to −86 | AGGAGATTCCA |
| mGM-CSF | −108 to −98 | AGGAGATTCCA |
| hIL-3 | −119 to −109 | TGGAGGTTCCA |
| mIL-3 | −115 to −105 | TGGAGGTTCCA |
| hG-CSF | −188 to −178 | CAGAGATTCCA |
| mG-CSF | −192 to −182 | CAGAGATTCCC |
| hγ-IFN | −163 to −153 | AGGAAACTCTA |
| mγ-IFN | −170 to −160 | AGGAAACTCTA |

Particularly preferred is use of the IL-2 enhancer region.

The enhancer region can be obtained by isolation and purification from a suitable genomic library, optionally using the conserved sequences set forth in Table 1 as identification probes. Alternatively, the conserved sequences themselves may be synthesized by well known means, such as using commercially available gene synthesizers, and incorporated into the DNA constructs by conventional means.

Suitable marker genes will upon expression provide a detectable signal which indicates that the CD28 transduction pathway of the T cell has been induced. Conveniently, a detectable signal will be visibly or optically detectable to facilitate screening of multiple samples simultaneously, for example using multiple-well microtiter plates. Particularly suitable are marker genes which produce a visible change within the culture media of the cultured cells, such as chromogenic (color) signals, fluorescent signals, luminescent signals, and the like. The use of the firefly luciferase (Luc) gene is described in detail in the Experimental section hereinafter. Other suitable marker genes include β-galactosidase and chloramphenicol acetyl-transferase.

The enhancer region and the marker gene will be incorporated into a suitable DNA construct by conventional recombinant DNA techniques in order to facilitate introduction into the starting T cell line. Usually, for easy construction, the DNA construct will be prepared from a bacterial plasmid where the enhancer, the marker gene, and usually a suitable promoter region, will be sequentially introduced in proper reading frame so that binding of the CD28 nuclear protein to the enhancer region will result in increased expression of the marker. The plasmid will usually include at least one antibiotic resistance gene to facilitate construction of the plasmid as well as screening of transfected T cell lines to identify those which have stably incorporated the plasmid DNA.

The DNA plasmid as a whole, or portions thereof including the enhancer, promoter, marker gene, and optionally antibiotic resistance gene, will be introduced by conventional transfection techniques into the starting T cell line. Suitable techniques include the use of reagents that improve chemical permeability, electroporation, and the like. After transfection, the T cells will be screened based on antibiotic resistance to identify those cells which have received the transfected DNA. The transfected cell lines will be further screened to confirm that stimulation of the CD28 receptor, for example with anti-CD28 antibody, results in expression of the marker phenotype, e.g. color, fluorescence, or luminescence. The transfected cell lines may be periodically tested over time in order to identify those where the DNA construct has been stably incorporated.

The construction of a suitable recombinant reporter plasmid containing nucleic acid sequences from −326 to +46 of the human IL-2 gene directing transcription of the firefly luciferase gene is described in Durand et al. (1988) Mol. Cell Biol. 8:1715–1724, the disclosure of which has been previously been incorporated herein by reference. The plasmid is designated pIL-2-Luc.

The Jurkat-IL2-Luc cell line described in the Experimental section hereinafter has achieved stable integration of the pIL2/L plasmid into the Jurkat genome for More than 3.5 years. The Jurkat-IL2-Luc cell line was derived by transfecting Jurkat cells with the pIL2/L plasmid by electroporation. Stable clonal transfectants were selected for long term (greater than one month) growth in G418. Clones which had appropriately integrated the plasmid construct were screened for their responsiveness to ionomycin and PMA. One such clone was designated Jurkat-IL2-Luc. This cell line was deposited with the American Type Culture Collection, 12301 Parklawn Drive, Rockville, Md., 20852, on Jun. 9, 1992, and carries the Accession Number CRL 11509.

Once a suitable modified T cell line has been obtained or established, screening assays of the present invention may be performed by culturing cells from the cell line under conditions which result in enhanced expression of the marker gene. Such conditions require activation or stimulation of both the T cell receptor (TCR) and the CD28 receptor. Stimulation of TCR can conveniently be provided by the addition of ionomycin at a concentration of about 0.5 μM to 1.0 μM, typically about 1 μM, and phorbol 12-myristate 13-acetate (PMA) at a concentration in the range from about 10 ng/ml to 50 ng/ml, usually about 50 ng/ml. These agents mimic the effect of TCR-induced phospholipase C activation by increasing the $Ca^{2+}$ concentration and activating protein kinase C, respectively. Other techniques for activating TCR include stimulation with anti-TCR antibodies, with lectins such as concanavalin A or phytohemagglutinin, or with staphylococcal enterotoxins. Activation of the CD28 receptor may be obtained by exposing the cells to anti-CD28 antibody. Suitable anti-CD28 antibodies can be obtained from hybridoma cell line MAb 9.3 (Hansen et al. (1980) Immunogenetics 10:247–252) or with other commercially available anti-CD28 antibodies, with antibodies typically being introduced at dilutions on the order of 1:10,000 of ascitic fluid or 10–1000 ng/ml of pure antibody. Other techniques for activating the CD28 receptor include stimulation with cell lines expressing the B7 antigen, with soluble B7 protein, or with B7 fusion proteins.

Test compounds will be added to the cultured cells, usually before induction of the marker gene by activation of TCR and the CD28 receptor, as described above. The test compounds can be any molecule, compound, or other substance which can be added to the cell culture without substantially interfering with cell viability. Suitable test compounds may be small molecules, biological polymers, such as polypeptides, polysaccharides, polynucleotides, and the like. Of particular interest will be small molecules, typically having a molecular weight below about 1000 daltons, usually having molecular weight below about 500 daltons, but may be as large as 10 kD in some instances. The test compound will typically be administered to the cell culture at a concentration in the range from about 1 nM to 1 mM, usually from about 1 µM to about 1 mM. Usually, the test results will be determined by comparing the level of marker gene expression in the absence of the test compound with the level of marker gene expression in the presence of the test compound. Test compounds which are effective in inhibiting the CD28 signal transduction pathway will cause a reduction in expression of the marker gene. While the quantitative reduction is not critical, the level of expression in the presence of effective test compounds will usually be no greater than 50% of the level of expression in the absence of test compound(s), more usually being no greater than 35%, and typically being no greater than 25%.

Test compounds which are found to be effective in inhibiting the CD28 signal transduction pathway in T cell culture will be considered as candidates for further determination of their ability to act as immunosuppressive in vitro or in vivo. Such further testing might comprise inhibition of in vitro responses, such as mixed leukocyte responses or antigen-induced proliferative responses, or of in vivo responses, such as allograft rejection or delayed-type hypersensitivity reactions in experimental animals.

The present invention further comprises pharmaceutical compositions incorporating effective test compound(s) selected by the above-described method and including a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable for delivering the compound(s) to an intended host. Sterile water, alcohol, fats, waxes, and inert solids may be used as the carrier. Pharmaceutically acceptable adjuvants, buffering agents, dispersing agents, and the like, may also be incorporated into the pharmaceutical compositions. Preparation of pharmaceutical compositions incorporating active agents is well described in the medical and scientific literature. See, for example, Remington's Pharmaceutical Sciences, Mack Publishing Company, Easton, Pa. 16th Edition, 1982, the disclosure of which is incorporated herein by reference.

The pharmaceutical compositions just described are suitable for systemic administration to the host, including both parental and oral administration. Parental administration includes subcutaneous, intravascular, and intravenous injection.

Concentrations of the compound in the pharmaceutical carrier may vary widely, i.e. from less than about 0.01% by weight of the composition to about 20% by weight, or greater. Typical pharmaceutical compositions for intravascular injection would be made up to contain, for example, about 1 to 4 ml of sterile buffer water and 1 µg to 1 mg of the compound identified by the method of the present invention. The typical composition for intravenous infusion could be made up to contain 100 to 500 ml of sterile Ringer's solution and about 1 to 100 mg of the compound.

The following examples are offered by way of illustration, not by way of limitation.

EXPERIMENTAL

Response of Jurkat-IL2-Luc to Stimulation.

A stable transfectant having a single copy of CD28RE, Jurkat-IL2-Luc (A.T.C.C. Accession No. CRL 11059), was stimulated with the treatment indicated in FIG. 1. After eight hours, the induced luciferase activity was assessed. Monoclonal antibody 9.3 react with CD28. The OKT8 monoclonal antibody serves as a specificity control. See FIG. 1.

Plasmid construction.

A duplex oligonucleotide corresponding to 3 repeated copies of the IL-2 CD28RE (−164 to −144) containing mutations within the AP1 site (−149 to −146) (Fraser et al. (1991) Science 251:313–316) was ligated to the 5'-end of a fragment containing −164 to +41 of the IL-2 promoter. This was ligated into the pXP2 luciferase (Nordeen (1988) Biotechniques 6:454–456) plasmid utilizing the Kpn1 and Hind3 sites. See FIG. 1.

Activity of the (CD28RE) 4X-Luc plasmid transiently transfected into Jurkat cells.

Figure 2:
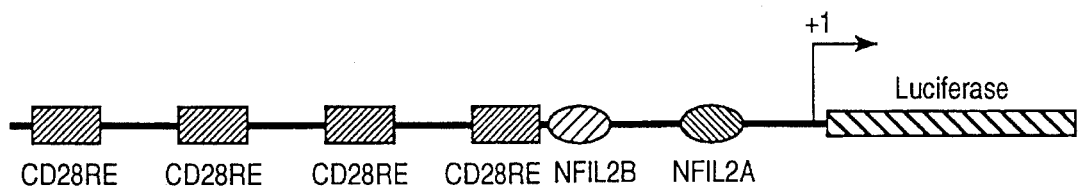
FIG. 2 illustrates the insertion of three repeat copies of IL-2 CD28RE and the IL-2 promoter into pXP2 luciferase, as described in the Experimental section.
Figure 3:
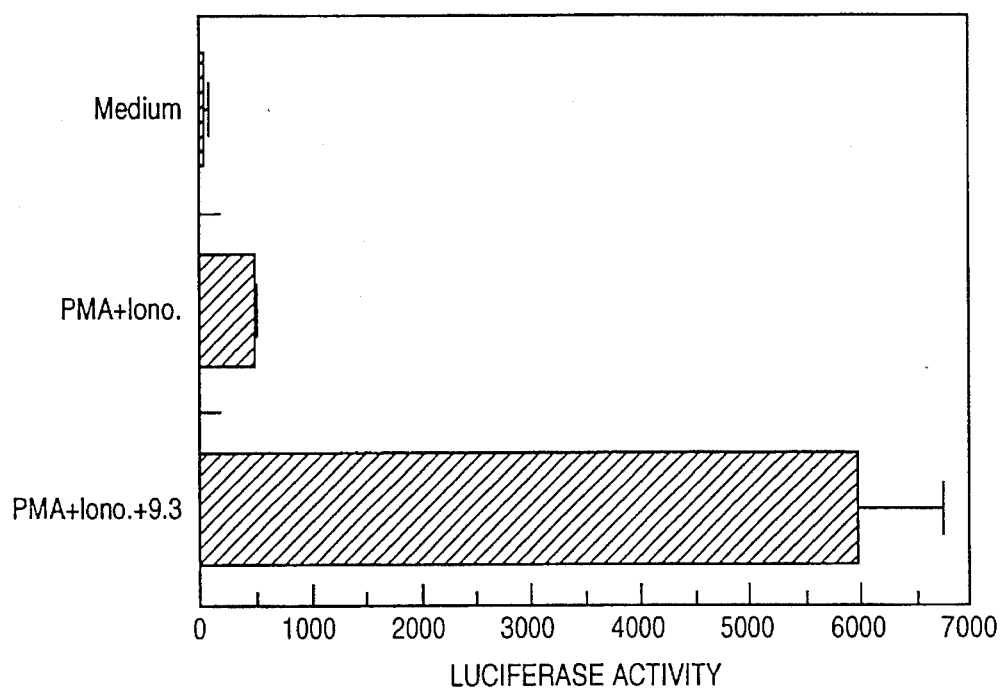
FIG. 3 illustrates the induction of luciferase activity in Jurkat cells transiently transfected with modified pXP2 luciferase shown in FIG. 2.

The plasmid construction was transiently transfected into Jurkat cells using the DEAE/dextran method. Cells were stimulated 20 hrs. later with the indicated stimuli and induced luciferase activity was assessed after 8 hours of stimulation. See. FIG. 2.

Although the foregoing invention has been described in some detail by way of illustration and example, for purposes of clarity of understanding, it will be obvious that certain changes and modifications may be practiced within the scope of the appended claims.

What is claimed is:

1. A method for screening test compounds for the ability to inhibit the CD28 signal transduction pathway in T cells, said method comprising:

exposing TCR-activated cultured T cells to conditions selected to induce the CD28 signal transduction pathway, wherein a DNA sequence comprising an enhancer region responsive to a CD28-regulated nuclear binding protein, a promoter, and a marker gene is stably incorporated in said T cells, and wherein said T cells are Jurkat-IL2-Luc cells, ATCC Accession No. CRL 11509;

administering test compounds to the cultured cells; and identifying which test compounds suppress expression of the marker gene.

2. A method as in claim 1 wherein the Jurkat-IL2-Luc cells are TCR-activated by exposure to ionomycin and PMA.

3. A method as in claim 1, wherein the CD28 signal transduction pathway is induced by exposure to anti-CD28 antibody.

4. A method as in claim 1, wherein the test compounds are small molecules having a molecular weight below 1000 daltons.

* * * * *